United States Patent
Jadhav et al.

(10) Patent No.: US 12,403,295 B2
(45) Date of Patent: Sep. 2, 2025

(54) FLUID CONNECTOR SYSTEM

(71) Applicant: CareFusion 303, Inc., San Diego, CA (US)

(72) Inventors: Amarsinh Deeliprao Jadhav, Hyderabad (IN); Mohamed Shafiq, Bangalore (IN); Kowshika K, Tirupur (IN)

(73) Assignee: CAREFUSION 303, INC., San Diego, CA (US)

( * ) Notice: Subject to any disclaimer, the term of this patent is extended or adjusted under 35 U.S.C. 154(b) by 112 days.

(21) Appl. No.: 18/342,085

(22) Filed: Jun. 27, 2023

(65) Prior Publication Data

US 2024/0050728 A1 Feb. 15, 2024

Related U.S. Application Data

(60) Provisional application No. 63/397,139, filed on Aug. 11, 2022.

(51) Int. Cl.
| | |
|---|---|
| *A61M 39/26* | (2006.01) |
| *A61M 39/10* | (2006.01) |
| *A61M 39/24* | (2006.01) |

(52) U.S. Cl.
CPC ............ *A61M 39/26* (2013.01); *A61M 39/10* (2013.01); *A61M 39/24* (2013.01); *A61M 2039/2433* (2013.01)

(58) Field of Classification Search
CPC .......... A61M 39/10; A61M 2039/1061; A61M 39/1011; A61M 39/24; A61M 2039/2433;
(Continued)

(56) References Cited

U.S. PATENT DOCUMENTS 5,713,856 A 2/1998 Eggers et al.
5,820,614 A * 10/1998 Erskine ............... F16L 55/1007
604/905
(Continued)

FOREIGN PATENT DOCUMENTS

EP 1678070 A2 7/2006
EP 1517723 B1 1/2007
(Continued)

OTHER PUBLICATIONS

International Search Report and Written Opinion for Application No. PCT/US2023/028479, dated Oct. 17, 2023, 16 pages.
(Continued)

*Primary Examiner* — David Colon-Morales
(74) *Attorney, Agent, or Firm* — MASCHOFF BRENNAN

(57) ABSTRACT

Fluid connector systems that can include first and second connectors that are couplable together to form a fluid pathway through the fluid connector system when the first and second connectors are coupled together, and can resist fluid flow through each of the first and second connectors when the first and second connectors are separated from each other, where the first and second connectors can include a valve within a channel and configured resist fluid flow through the respective first or second connector in an closed position and to reduce the resistance to fluid flow through the first or second connector in an open position, and the first and second connectors including one or more arm configured to engage each other to form a snap fitting feature that can resist separation therebetween.

19 Claims, 6 Drawing Sheets

(58) Field of Classification Search
CPC ............. A61M 39/26; A61M 2039/267; F16L 37/0985; F16L 37/40; F16L 55/1015
See application file for complete search history.

(56) References Cited

U.S. PATENT DOCUMENTS

| | | | |
|---|---|---|---|
| 6,171,287 B1 * | 1/2001 | Lynn | A61M 39/162 604/905 |
| 6,874,522 B2 | 4/2005 | Anderson et al. | |
| 7,004,934 B2 | 2/2006 | Vaillancourt | |
| 7,040,598 B2 | 5/2006 | Raybuck | |
| 7,153,296 B2 | 12/2006 | Mitchell | |
| 7,350,764 B2 | 4/2008 | Raybuck | |
| 7,396,051 B2 | 7/2008 | Baldwin et al. | |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | Mcmichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,758,307 B2 * | 6/2014 | Grimm | A61M 5/385 604/247 |
| 8,777,908 B2 | 7/2014 | Fangrow, Jr. | |
| 8,777,909 B2 | 7/2014 | Fangrow, Jr. | |
| 8,795,256 B1 | 8/2014 | Smith | |
| 8,888,758 B2 | 11/2014 | Mansour | |
| 8,899,267 B2 * | 12/2014 | Diodati | A61M 39/18 137/614.04 |
| 8,910,919 B2 | 12/2014 | Bonnal et al. | |
| 8,974,425 B2 | 3/2015 | Tachizaki et al. | |
| 8,974,437 B2 * | 3/2015 | Williams | A61M 39/26 604/533 |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,192,753 B2 | 11/2015 | Lopez et al. | |
| 9,234,616 B2 | 1/2016 | Carrez et al. | |
| 9,358,379 B2 | 6/2016 | Fangrow, Jr. | |
| 9,433,769 B2 | 9/2016 | Bayly | |
| 9,468,749 B2 | 10/2016 | Mansour et al. | |
| 9,492,649 B2 | 11/2016 | Carrez et al. | |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,933,094 B2 * | 4/2018 | Fangrow | A61M 39/1011 |
| 9,974,939 B2 | 5/2018 | Fangrow, Jr. | |
| 9,974,940 B2 | 5/2018 | Fangrow, Jr. | |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,207,100 B2 * | 2/2019 | Harton | A61M 39/1055 |
| 10,315,025 B2 * | 6/2019 | Phillips | A61M 39/26 |
| 10,398,887 B2 | 9/2019 | Fangrow, Jr. et al. | |
| 10,441,507 B2 | 10/2019 | Sanders | |
| 10,518,078 B2 | 12/2019 | Stjernberg Bejhed et al. | |
| 10,569,073 B2 | 2/2020 | Hallisey et al. | |
| 10,625,068 B2 | 4/2020 | Leuthardt et al. | |
| 10,625,071 B2 * | 4/2020 | Bonnal | A61M 39/26 |
| 10,655,768 B2 * | 5/2020 | Jones | A61M 39/24 |
| 10,697,570 B2 | 6/2020 | Fangrow | |
| 10,744,315 B2 | 8/2020 | Sanders | |
| 10,842,982 B2 | 11/2020 | Fangrow, Jr. | |
| 10,857,346 B2 | 12/2020 | Dennis et al. | |
| 10,864,362 B2 * | 12/2020 | Jones | A61M 39/1011 |
| 10,881,847 B2 | 1/2021 | Lynn | |
| 11,168,818 B2 | 11/2021 | Fangrow | |
| 11,207,514 B2 | 12/2021 | Kakinoki | |
| 11,235,135 B2 | 2/2022 | Tsai | |
| 11,273,297 B2 | 3/2022 | Kakinoki | |
| 11,484,471 B2 | 11/2022 | Sanders | |
| 11,491,084 B2 | 11/2022 | Ueda et al. | |
| 2004/0215158 A1 | 10/2004 | Anderson | |
| 2005/0090805 A1 | 4/2005 | Shaw et al. | |
| 2006/0129109 A1 * | 6/2006 | Shaw | A61M 39/26 604/246 |
| 2007/0088292 A1 | 4/2007 | Fangrow, Jr. | |
| 2007/0088293 A1 | 4/2007 | Fangrow, Jr. | |
| 2007/0088294 A1 | 4/2007 | Fangrow, Jr. | |
| 2007/0225635 A1 | 9/2007 | Lynn | |
| 2008/0039803 A1 | 2/2008 | Lynn | |
| 2011/0106046 A1 | 5/2011 | Hiranuma | |
| 2014/0249487 A1 | 9/2014 | Lynn | |
| 2014/0330254 A1 | 11/2014 | Rosenberger et al. | |
| 2015/0157849 A1 | 6/2015 | Phillips et al. | |
| 2015/0238750 A1 | 8/2015 | Williams et al. | |
| 2016/0000363 A1 | 1/2016 | Jones et al. | |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsai | |
| 2021/0077803 A1 | 3/2021 | Lynn | |
| 2021/0252267 A1 | 8/2021 | Fangrow, Jr. | |
| 2021/0388926 A1 | 12/2021 | Martin et al. | |
| 2021/0393938 A1 | 12/2021 | Lynn et al. | |
| 2022/0260189 A1 | 8/2022 | Deuse | |
| 2022/0282814 A1 | 9/2022 | Fangrow | |

FOREIGN PATENT DOCUMENTS

| | | | |
|---|---|---|---|
| EP | 1622675 B1 | 8/2009 | |
| EP | 2144634 A1 | 1/2010 | |
| EP | 2298407 A1 | 3/2011 | |
| EP | 2694132 A1 | 2/2014 | |
| EP | 2562456 B1 | 6/2014 | |
| EP | 2782633 A1 | 10/2014 | |
| EP | 1842002 B1 | 4/2015 | |
| EP | 2736582 B1 | 5/2015 | |
| EP | 2089094 B1 | 1/2016 | |
| EP | 2219721 B1 | 12/2017 | |
| EP | 2753396 B1 | 12/2017 | |
| EP | 2736584 B1 | 4/2018 | |
| EP | 3305361 A1 | 4/2018 | |
| EP | 2271398 B1 | 11/2018 | |
| EP | 2480281 B1 | 11/2018 | |
| EP | 2790750 B1 | 11/2018 | |
| EP | 2331191 B1 | 3/2019 | |
| EP | 3079756 B1 | 3/2019 | |
| EP | 2121114 B1 | 5/2019 | |
| EP | 2719419 B1 | 5/2019 | |
| EP | 2956204 B1 | 8/2019 | |
| EP | 3421077 B1 | 8/2019 | |
| EP | 3530313 A1 | 8/2019 | |
| EP | 3538201 A1 | 9/2019 | |
| EP | 3570807 A1 | 11/2019 | |
| EP | 3570809 A1 | 11/2019 | |
| EP | 2536463 B1 | 4/2020 | |
| EP | 3381505 B1 | 5/2020 | |
| EP | 3538201 B1 | 5/2020 | |
| EP | 1904152 B1 | 12/2020 | |
| EP | 2150307 B1 | 12/2020 | |
| EP | 3313490 B1 | 1/2021 | |
| EP | 3760275 A1 | 1/2021 | |
| EP | 3851155 A1 | 7/2021 | |
| EP | 3517164 B1 | 9/2021 | |
| EP | 3954355 A1 * | 2/2022 | A61J 1/2055 |
| EP | 3960229 A1 | 3/2022 | |
| EP | 3973044 A1 | 3/2022 | |
| EP | 3305361 B1 | 5/2022 | |

(56) References Cited

FOREIGN PATENT DOCUMENTS

| EP | 3134052 B1 | 8/2022 | | |
|---|---|---|---|---|
| EP | 3530313 B1 | 8/2022 | | |
| WO | WO-2010127461 A1 | * | 11/2010 | .......... A61M 1/0025 |
| WO | WO-2021099437 A1 | | 5/2021 | |
| WO | WO-2021180675 A1 | | 9/2021 | |
| WO | WO-2021252197 A1 | | 12/2021 | |
| WO | WO-2022042956 A1 | | 3/2022 | |
| WO | WO-2022149339 A1 | * | 7/2022 | ............ A61M 39/10 |
| WO | WO-2022207560 A1 | | 10/2022 | |

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 5/21 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group Ab, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

* cited by examiner

FLUID CONNECTOR SYSTEM

CROSS REFERENCE TO RELATED APPLICATION

This application claims the benefit of priority under 35 U.S.C. § 119 to U.S. Provisional Patent Application Ser. No. 63/397,139, entitled "FLUID CONNECTOR SYSTEM," filed on Aug. 11, 2022, the entire contents of which is incorporated herein by reference.

BACKGROUND

The present disclosure relates generally to medical fluid connectors and, more particularly, to self-sealing fluid connector systems having first and second connectors that can be coupled together to form a fluid pathway and to obstruct the fluid pathway upon separation of the first and second connectors.

Medical connections are widely used in fluid delivery systems such as those used in connection with intravenous (IV) fluid lines, blood access, hemodialysis, peritoneal dialysis, enteral feeding, drug vial access, and other procedures.

In some instances, the medical connection can become dislodged or disconnected in an unintended manner. For example, medical tubing of an IV set that is coupled to a catheter can become dislodged when an unintended or unexpected forces is exerted upon the catheter, which may exceed the design limitations of the catheter securement method. An unintended or unexpected force can be applied to the tubing and/or catheter when the patient moves or rolls over within a bed, or when the tubing or another portion of an intravenous set become caught on a portion of the bed, such as the railing, or when a patient is panicking, disoriented, or fidgeting to such an extent that the medical tubing is unintentionally or intentionally pulled away from the patient or away from the medical equipment coupled to the tubing.

SUMMARY

In accordance with at least some embodiments disclosed herein is the realization that unintended dislodgement or disconnection of a medical connection, such as a medical fluid line, can result in injury to a patient or a caregiver, such as by depriving the patient of a medicament, increasing the potential for infection to the patient, and exposing the caregiver to harmful medicaments.

Accordingly, aspects of the present disclosure provide fluid connector system comprising a first connector and a second connector, the first connector comprising a housing having a proximal end and a distal end, an inner surface forming a housing channel extending between a proximal opening and a distal opening of the housing, and a first valve positioned in the housing channel, and the second connector comprising a body having a proximal end and a distal end, an inner surface forming a body channel extending between a proximal opening and a distal opening of the body, and a second valve positioned in the body channel, wherein an outer surface of the distal end of the body forms a protrusion and one or more arm, wherein the one or more arm extends along the protrusion, and wherein, when the first and second connectors are coupled together, the one or more arm is engaged against the housing to resist separation of the first and second connectors, and the protrusion extends to the proximal opening of the housing to engage against the first valve and open a fluid passageway through the first and second connectors.

In some instances, the present disclosure includes a method for providing a fluid connector system, the method comprising providing a first connector comprising a housing having a proximal end and a distal end, an inner surface forming a housing channel extending between a proximal opening and a distal opening of the housing, and a first valve positioned in the channel of the housing, and providing a second connector comprising a body having a proximal end and a distal end, an inner surface forming a body channel extending between a proximal opening and a distal opening of the body, and a second valve positioned in the channel of the body, wherein an outer surface of the distal end of the body forms a protrusion and one or more arm, wherein the one or more arm extends along the protrusion, wherein the first and second connectors are couplable together such that the one or more arm engages against the housing and the protrusion extends to the proximal opening of the housing to engage against the first valve and open a fluid passageway through the first and second connectors.

Accordingly, the present application addresses several operational challenges encountered in prior fluid connections and provides numerous improvements that enable the user to increase safety and efficacy, while more easily and precisely providing fluid connections.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a fluid connector system. The fluid connector system can provide for efficient and safe maintenance of fluid connections, such as the connections used for transferring medical fluids toward or away from a patient. The fluid connector system can maintain a fluid pathway by resisting unintended disconnection when a pulling or tension force is applied to the fluid connector system, such as when a patient moves or when the medical tubing is pulled away from the patient.

The fluid connector system can also prevent injury to a patient or a caregiver by permitting disconnection or separation between portions of the connector system when a pulling or tension force exceeds a threshold. The fluid connector system can also prevent injury to a patient or a caregiver by obstructing the fluid pathway when disconnection or separation between portions of the connector system occurs. Further, the fluid connector system can provide for efficient and safe reestablishment of the fluid pathway, by permitting reassembly of portions of the system after a disconnection or separation occurs.

Figure 1:
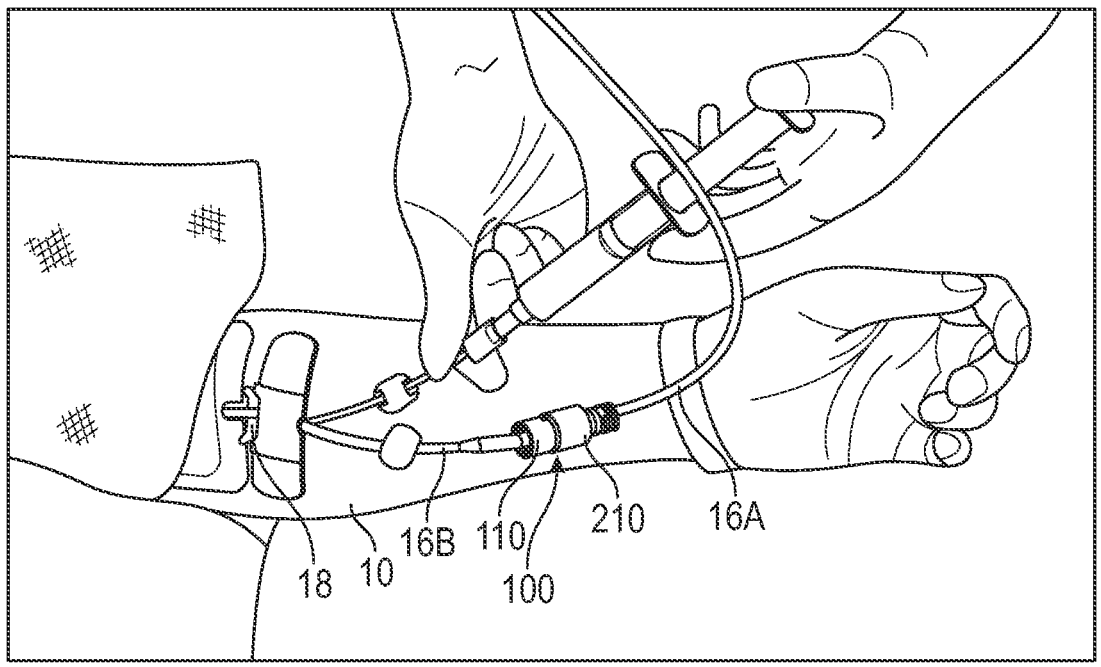
FIG. 1 illustrates a fluid connector system in use with an IV set coupled to a patient, in accordance with aspects of the present disclosure.

Referring now to the figures, FIG. 1 illustrates an example of a fluid connector system in use in accordance with aspects of the present disclosure. The fluid connector system 100 is coupled with tubing of an IV set, which is being used to direct a fluid to a patient 10. The IV set can include a first length of tubing 16A that is Coupled to a first portion of the fluid connector system 100, and a second length of tubing 16B that is coupled to fluid connector system 100 and extends to an IV catheter 18.

The fluid connector system 100 couples the first and second lengths of tubing 16A, 16B to the IV catheter 18 so that a fluid can move through the tubing 16A, 16B and the IV catheter 18 by flowing through the fluid connector system 100. If a sufficient pulling or tension force is applied to the fluid connector system 100, such as when a patient moves or when the medical tubing is pulled away from the patient, portions of the fluid connector system 100 can separate from each other to separate the first length of tubing 16A from the patient and resist fluid flow out of the first length of tubing 16A and out of the second length of tubing 16B.

Although the fluid connector system 100 is illustrated being coupled along a fluid pathway of an IV set, it should be understood that the fluid connector system 100 can be connected within other fluid pathways, such as between a patient and a IV pump or between a patient and a dialysis machine. The fluid connector system 100 can also be connected along another portion of a fluid pathway. For example, the fluid connector system 100 can be connected along a proximal portion of the fluid pathway, such as being connected between the tubing 16 and the medicament bag 12 or other fluid therapy device. In another example, any of the first and second portions of the fluid connector system 100 can be directly coupled to another fluid delivery devices, such as the catheter or a medicament bag.

Figure 2:
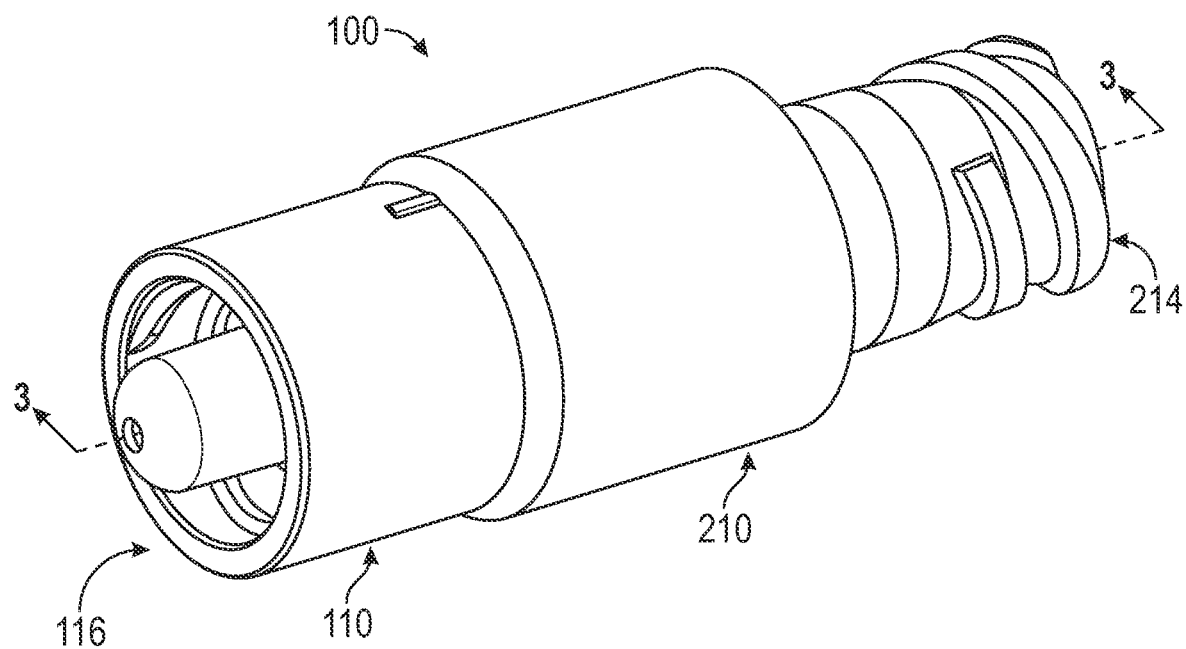
FIG. 2 illustrates a perspective view of an embodiment of a fluid connector system, in accordance with aspects of the present disclosure.

The portions of the fluid connector system 100 that are separable from each other include a first connector 110 and a second connector 210, which are illustrated in FIGS. 1 and 2. The first and second connectors 110, 210 can be coupled together by engaging a portion of the second connector 210 against a portion of the first connector 110. When the first and second connectors 110, 210 coupled together, a fluid channel of each of the first and second connectors 110, 210 is coupled together to form a fluid pathway through the fluid connector system 100.

The first and second connectors 110, 210 resist unintended separation from each other. However, if any of the first connector 110 and the second connector 210 are separated from each other, such as when a pulling or tension force on the fluid connector system 100 exceeds a threshold, the first connector 110 and the second connector 210 can separate from each other while maintaining the ability to reconnect the first and second connectors 110, 210 together. In some embodiments of the present disclosure, the threshold force for separating the first and second connectors 110, 210 is greater than or equal to approximately five pounds (22.25 Newtons).

Figure 3:
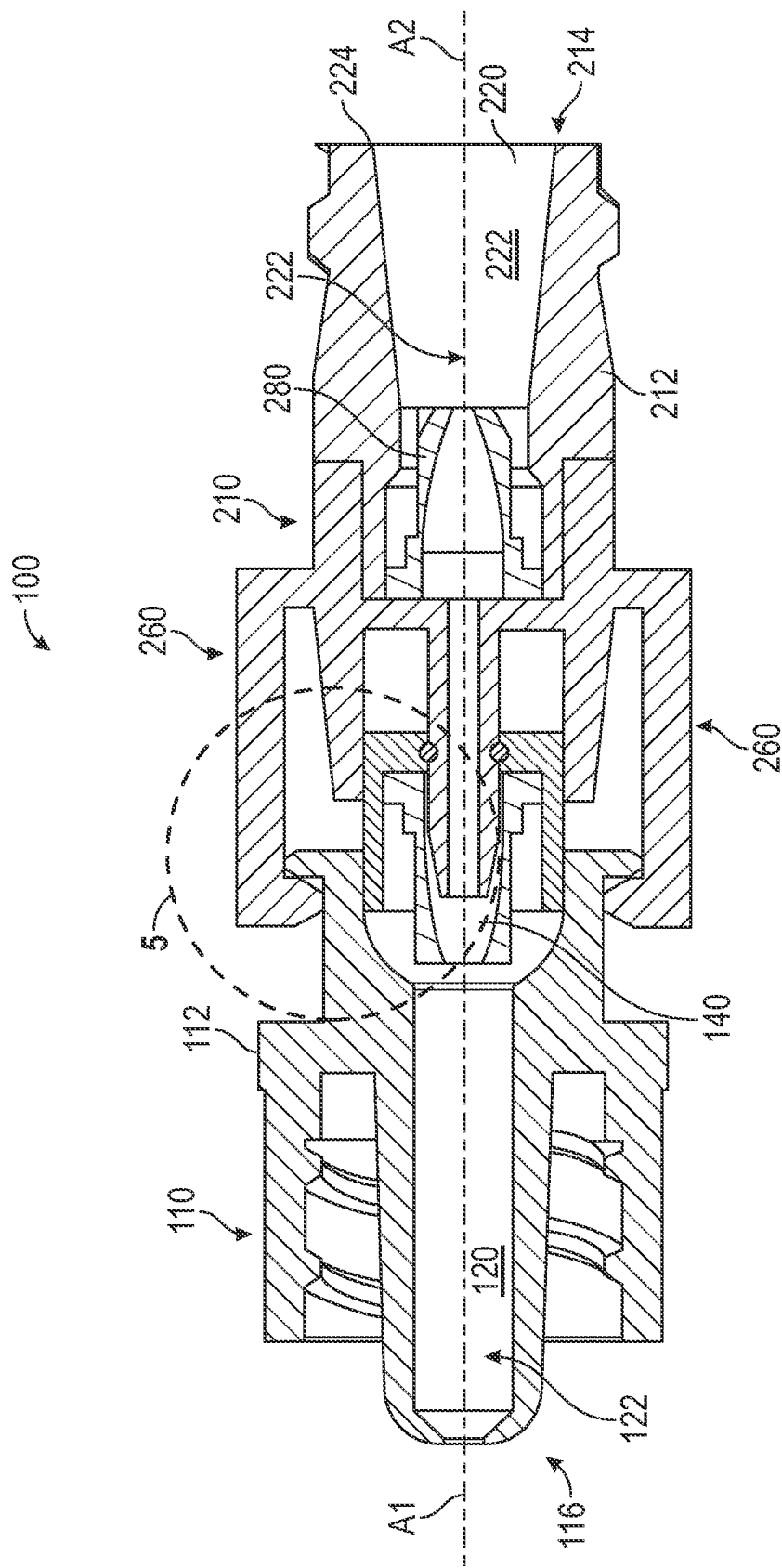
FIG. 3 illustrates a cross-sectional view of the fluid connector system of FIG. 2, in accordance with aspects of the present disclosure.

When the first and second connectors 110, 210, separate from each other, as illustrated in FIG. 3, the respective first and second connectors 110, 210 can resist a fluid flow therethrough. In some embodiments of the present disclosure, each of the first and second connectors 110, 210 can resist fluid flow by obstructing a fluid passage through their respective assemblies.

The first connector 110 includes a housing 112 having a proximal end 114, a distal end 116, and an inner surface 120 forming a housing channel 122 extending between a proximal opening 124 at the proximal end 114 of the housing and a distal opening 126 at the distal end 116 of the housing. A proximal end of the housing 112, forming the proximal end 114 and the proximal opening 124, is configured to removable couple with the second connector 210.

Figure 4:
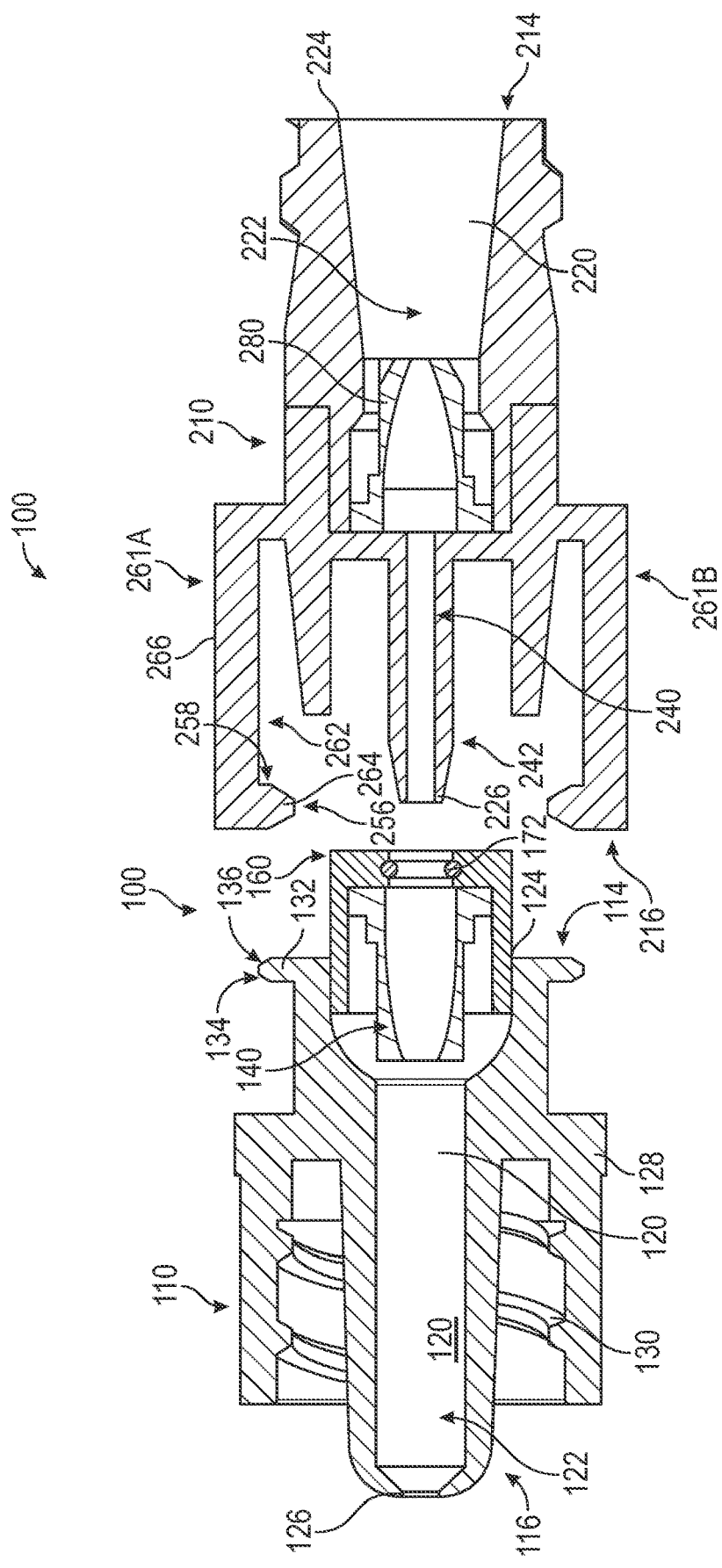
FIG. 4 illustrates a cross-sectional view of the fluid connector system of FIG. 2, in accordance with aspects of the present disclosure.

A first valve 140 is positioned in the housing channel 122 to resist or permit a fluid flow through the housing channel 122. When the first connector 110 is not coupled with the second connector 210 or another mating connector, as shown in FIG. 4, the first valve 140 is in a closed position. In the closed position, the housing channel 122 is obstructed by the first valve 140 to resist fluid flow through the first connector 110.

When the first connector 110 is coupled with the second connector 210, as shown in at least FIGS. 2 and 3, the first valve 140 is moved to an open position. In the open position, the first valve 140 is configured to impart no resistance, or less resistance relative to the opening position of the first valve 140. Thus, in the open position of the first valve 140, the housing channel 122 is unobstructed to permit a fluid flow through the first connector 110.

The first valve 140 of the first connector can be configured as a check valve that can permit a fluid to move through the first valve 140 in an open position, and can resist movement of the fluid through the first valve 140 in an closed position. In the open position, the first valve 140 does not resist movement of a fluid in a direction from the proximal end 114 toward the distal end 116 of the housing, and in the closed position, the first valve 140 resists movement of a fluid in a direction from the distal end 116 toward the proximal end 114 of the housing.

The first valve 140 is shaped, in some embodiments, as a duck-billed check valve; however, the present disclosure contemplates that the first valve 140 can be configured as check valve having another shape or structure.

The second connector 210 includes a body 212 having a proximal end 214, a distal end 216, and an inner surface 220 forming a body channel 222 extending between a proximal opening 224 at the proximal end 214 of the housing and a distal opening 226 at the distal end 216 of the body.

A portion of the body 212, including the distal end 216 and the distal opening 226, forms a protrusion 240 and one or more arm 260, where the protrusion 240 is configured to extend toward the proximal opening 124 of the housing and the one or more arm 260 is configured to engage against the housing 112 when the first and second connectors 110, 210 are coupled together.

The protrusion 240 is also configured to form a portion of the fluid passageway through the second connector 210, and therefore, the inner surface 220 of the body 212 forms a portion of the body channel 222 through the protrusion 240. The body channel 222 extends to the distal opening 226 of the body, which is located at a distal end portion of the protrusion 240. In some embodiments of the present disclosure, the distal opening 226 is located at a distal-most end of the protrusion 240; however, it should be understood that the present disclosure contemplated embodiments in which the distal opening 226 is positioned along another portion of the protrusion 240. For example, in some embodiments of the present disclosure, the distal opening 226 is located between a proximal and distal ends of the protrusion 240.

The one or more arm 260 extends in a direction away from the proximal end 214 of the body such that, when the first and second connectors 110, 210 are coupled together, a portion of the one or more arm 260 engages against the housing 112 of the first connector to resist movement of the first and second connectors 110, 210 in a direction away from each other. Engagement of the one or more arm 260 against the housing 112 can, in some instances of the present disclosure, define a snap fitting or snap joint between the first and second connectors 110, 210.

The one or more arm 260 includes an inner surface 262 that is spaced apart from the outer surface 242 of the protrusion by a distance to permit a portion of the first connector 110 to be positioned between the protrusion 240 and the one or more arm 260 when the first and second connectors 110, 210 are coupled together.

To resist movement of the first and second connectors 110, 210 in a direction away from each other, the one or more arm 260 can include a ridge 264 at a distal end portion 266 of the one or more arm. To resist movement of the first and second connectors 110, 210, the ridge 264 is configured to engage against the first connector 110. To engage against the first connector 110, the ridge 264 extends radially inward in a direction toward the protrusion 240 of the second connector.

Although the ridge 264 is configured to resist separation of the first and second connectors 110, 210, the one or more arm 260 is also configured to permit separation of the first and second connectors 110, 210 when a threshold force exceeded between the first and second connectors 110, 210. Separation of the first and second connectors 110, 210 can occur when the one or more arm 260 is biased or flexed in a direction away from the protrusion 240.

the one or more arm 260, or the distal end portion 266 of the one or more arm, is caused to bias or flex by engagement of the ridge 264 against the housing 112 when the first and second connectors 110, 210 are moved away from each other.

In some embodiments of the present disclosure, the one or more arm 260 comprises a first arm 261A and a second arm 261B. As illustrated, for example, FIGS. 3 and 4 the first and second arms 261A, 261B can be spaced apart from each other around a longitudinal axis A2 extending between the proximal and distal ends of the body.

Figure 6:
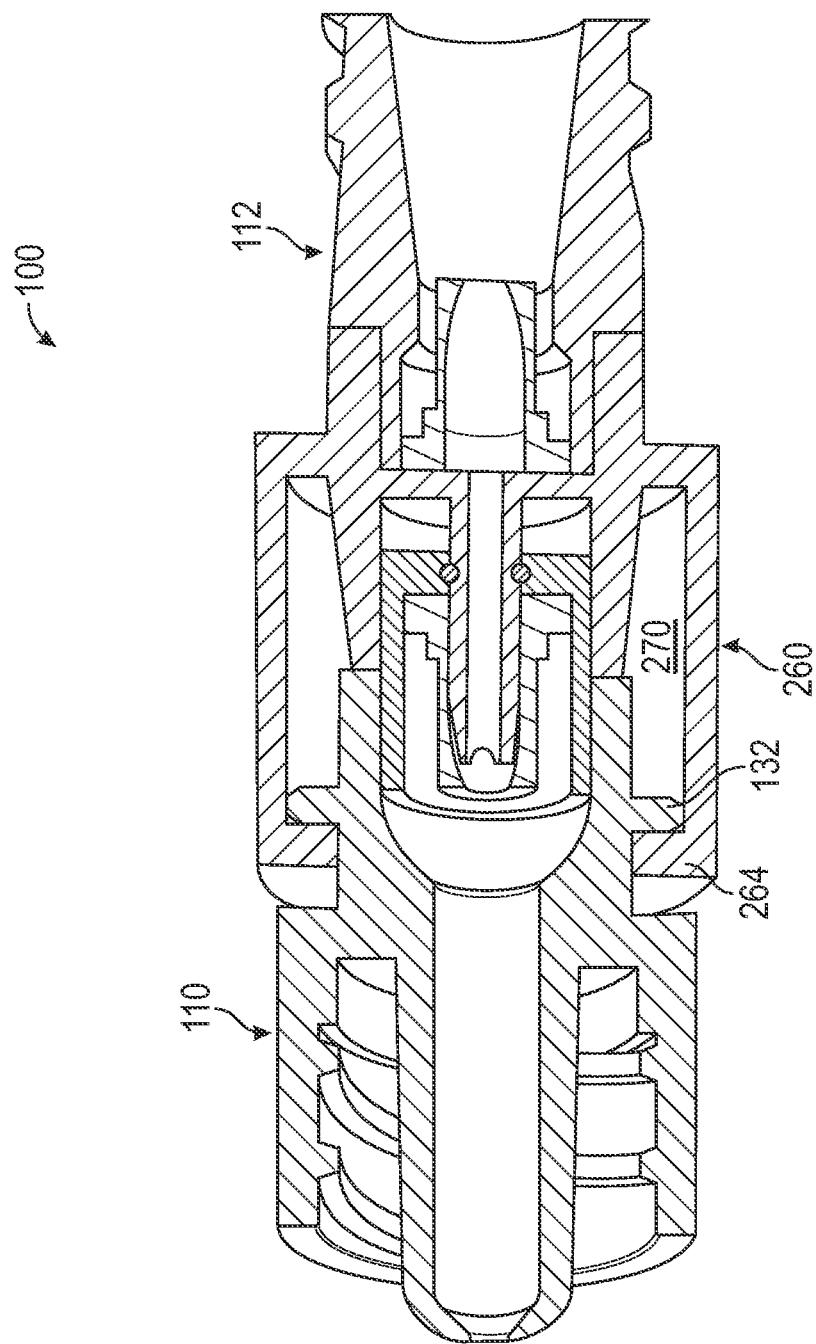
FIG. 6 illustrates a cross-sectional view of another embodiment of a fluid connector system, in accordance with aspects of the present disclosure.

In some embodiments of the present disclosure, the one or more arm 260 is shaped as a continuous or semi-continuous circumferential wall 270 extending around a longitudinal axis A2, as illustrated, for example, FIGS. 2 and 6. In some instances of the present disclosure, the first and second arms 261A, 261B can be defined by the circumferential wall 270 having one or more channel extending therethrough.

A second valve 280 is positioned in the body channel 222 to resist a fluid flow through the body channel 222 in the closed position, and permit fluid flow through the body channel 222 in the open position. In some embodiments, of the present disclosure, the second valve 280 is in the closed position when the second connector 210 is not coupled with the first connector 110, and is moved to the open position when the first and second connectors are coupled together. In some embodiments, the second valve 280 is moved from the closed to the open position by pressure of a fluid in the body channel 222.

The second valve 280 can be configured as a check valve that can permit a fluid to move through the second valve 280 in an open position, and can resist movement of the fluid through the second valve 280 in an closed position. In the open position, the second valve 280 does not resist movement of a fluid between the proximal end 214 and the distal end 216 of the body, and in the closed position, the second valve 280 resists movement of a fluid between the proximal end 214 and the distal end 216 of the body.

The second valve 280 is shaped, in some embodiments, as a duck-billed check valve; however, the present disclosure contemplates that the second valve 280 can be configured as check valve having another shape or structure.

In some embodiments of the present disclosure, any of the distal opening 126 of the first connector and the proximal opening 224 of the second connector can be configured as any of a male and female luer.

In some embodiments, a distal end portion of the housing 112 that forms the distal opening 126 can have an outer surface shaped as a male luer, and a proximal end portion of the body 212 that forms the proximal opening 224 can be shaped as a female luer. Any of the male and female luer can be configured to couple with any of a tubing or moating connector.

To couple with a tubing or mating connector, the first connector 110 and/or second connector 210 forming the male luer also includes a sleeve 128 having an inner surface that is spaced apart from the outer surface of the male luer. The sleeve 128 is configured to engage against a mating connector coupled to the male luer. In some instances of the present disclosure, the sleeve 128 includes a thread 130 extending along an inner surface of the sleeve and configured to mate with a thread of the mating connector. In some instances, the present disclosure also contemplates that the sleeve 128 can be configured to couple with a mating connector using an interference fit therebetween, or using another mating structure, such as a notch and groove.

In some embodiments of the present disclosure, the first connector 110 can also include an insert 160 coupled to the proximal opening 124 and configured to retain the first valve 140 with the housing 112. The features of 110, the insert 160 can include a first end 162, a second end 164, an inner surface 166 forming a cavity 168 extending into the second end 164, and a passage 170 extending through the first end 162 and intersecting the cavity 168.

The first valve 140 is positioned between the insert 160 and the housing 112, and is oriented adjacent to the passage 170. In some embodiments of the present disclosure, a first portion of the first valve 140 is positioned within the cavity 168 of the insert, and a second portion of the first valve 140 is positioned within the housing channel 122. Additionally, a portion of the first valve 140 can intersect a passageway defined between the passage 170 and the housing channel 122.

When coupled to the proximal opening 124 of the housing, the first end 162 of the insert can receive a portion of the second connector 210 through the passage 170 to form a portion of the fluid passageway through the fluid connector system 100. To prevent leakage or a contaminant from moving between the first and second connectors 110, 210, and into the fluid passageway through the fluid connector system 100, a seal 172 is positioned along the passage 170 of the insert. It should be understood, however, that although a seal 172 is disclosed herein, the present disclosure contemplates that a seal between the first and second connectors 110, 210, or between features of each of the first and second connectors 110, 210, by an interference fit, a sealant substance, or an adhesive.

Figure 5:
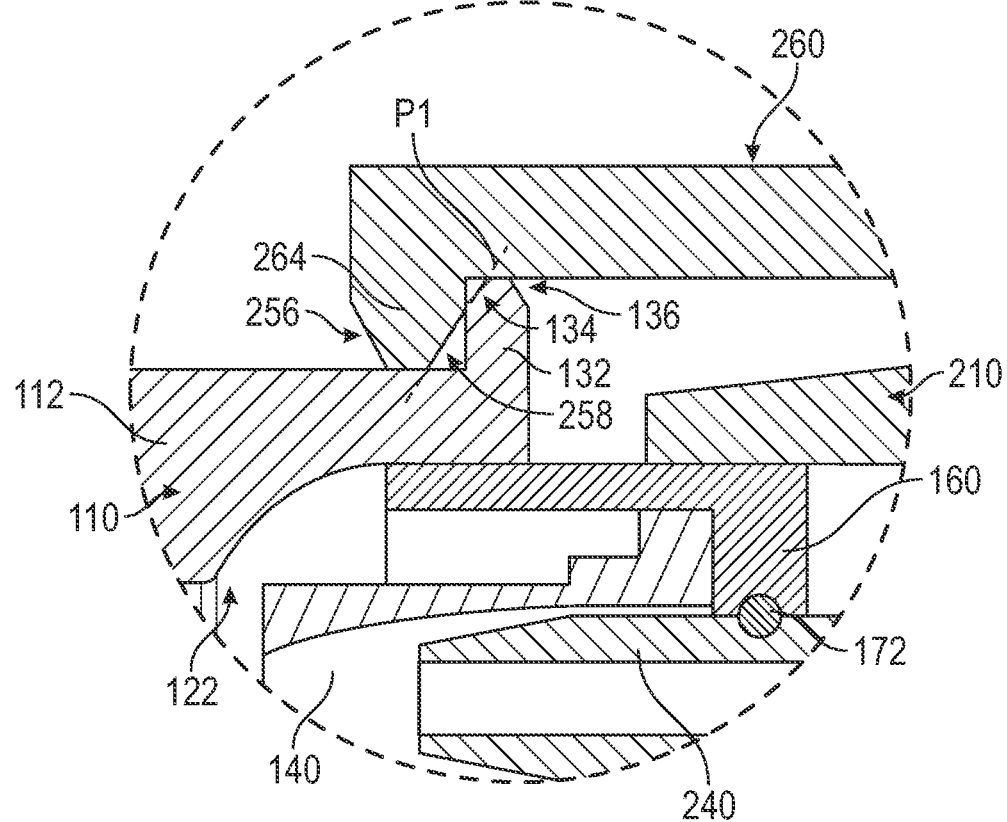
FIG. 5 illustrates a detail view of the fluid connector system of FIG. 3, in accordance with aspects of the present disclosure.

A detail view of the interface between the one or more arm 260 of the body 212 of the second connector and the housing 112 of the first connector is illustrated in the detail view of FIG. 5. The interface between the one or more arm 260 and the housing 112 can be defined by engagement of the ridge 264 of the one or more arm against a flange 132 of housing 112.

The flange 132 can be located along a portion of the housing 112 forming the proximal end 114 and the proximal opening 124. When the first and second connectors 110, 210 are coupled together, the ridge 264 is positioned between the flange 132 and the distal end 116 of the housing.

Although in some embodiments of the present disclosure, the flange 132 is configures to extend radially outward in a direction away from a longitudinal axis A1 extending between the proximal and distal ends of the housing, the present disclosure contemplates other structures to resist movement of the one or more arm 260. In some embodiments of the present disclosure, the first connector 110 can include a structure to resist movement of the one or more arm 260 of the second connector, including, for example, a channel that extends into the outer surface of the housing 112 and is configured to receive the ridge 264 therein.

FIG. 5 also illustrates embodiments of the present disclosure in which the flange 132 comprises a distal-facing surface 134 and a proximal-facing surface 136, and the ridge 264 comprises a distal facing surface 256 and a proximal-facing surface 258.

When are moved in a direction toward each other, the distal facing surface 256 of the ridge can engage against the proximal-facing surface 136 of the flange. Engagement of the distal facing surface 256 of the ridge against the proximal-facing surface 136 of the flange can cause the one or more arm 260 to bias or flax radially outward, thereby permitting the first and second connectors 110, 210 to be moved further toward each other.

When the first and second connectors 110, 210 are moved toward each other by a distance such that the ridge is distal to the flange 132, the one or more arm 260 can move radially inward to a less-biased or less-flexed position.

When the first and second connectors 110, 210 are coupled together, the distal-facing surface 134 of the flange can be aligned with the proximal-facing surface 258 of the ridge such that a common plane P1 extends along each of the distal-facing surface 134 and the proximal-facing surface 258.

The common plane P1 can be configured by forming the distal-facing surface 134 of the flange at a first angle, relative to the longitudinal axis A1, and the proximal-facing surface 258 of the ridge at a second angle, relative to the longitudinal axis A2. In some aspects of the present disclosure, the first and second angles are approximately 40 degrees relative to the longitudinal axis A1 of the housing 112. The first and second angles can, in some instances, be selected to increase or decrease resistance to assembly and separation between the first and second connectors 110, 210.

The resistance or force to assembly and separation between the first and second connectors 110, 210, as a result of the first and second angles, can be configured so that the force required for assembly of the first and second connectors 110, 210 is less than the force required for separation the first and second connectors 110, 210. In some embodiments of the present disclosure, the force required to cause deflection or biasing of the one or more arm such that the first and second connectors 110, 210 are separable is approximately two time greater that the force required to cause deflection or biasing of the one or more arm such that the first and second connectors 110, 210 can be coupled together.

Although in some embodiments of the present disclosure, the first and second angles can provide a common plane P1 between the distal-facing surface 134 and the proximal-facing surface 258, the present disclosure also contemplates embodiments in which each of the distal-facing surface 134 and the proximal-facing surface 258 define a plane that does not intersect.

Figure 7:
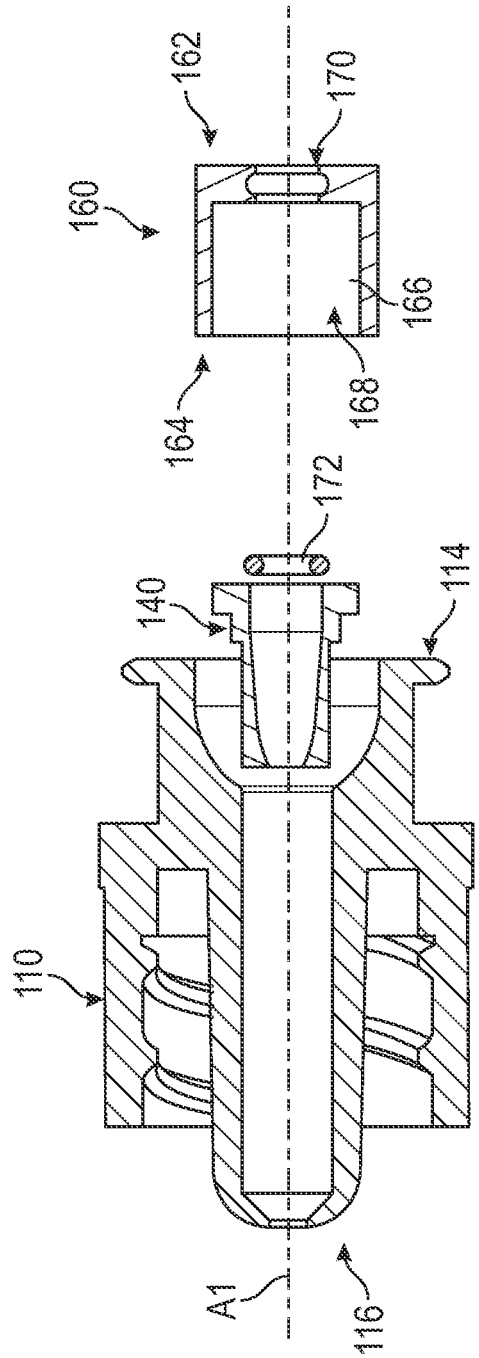
FIG. 7 illustrates an exploded cross-sectional view of a first connector of the fluid connector system, in accordance with aspects of the present disclosure.

Assembly of embodiments of the first and second connectors 110, 210 is illustrated in Figured 7 and 8, respectively. Referring to FIG. 7, the first connector 110 can be assembled by inserting the first valve 140 into the proximal opening 124 of the housing 112. The insert 160 can be moved toward the proximal end 114 of the housing with the first valve 140 therebetween. In some embodiments of the present disclosure, the first valve 140 is retained in the first connector 110 when the second end 164 of the insert is coupled to the proximal end 114 of the housing 112. The seal 172 of the first connector can be inserted into the passage 170, and in some embodiments, the insert 160 can include a groove configured to receive the seal 172 therein.

Figure 8:
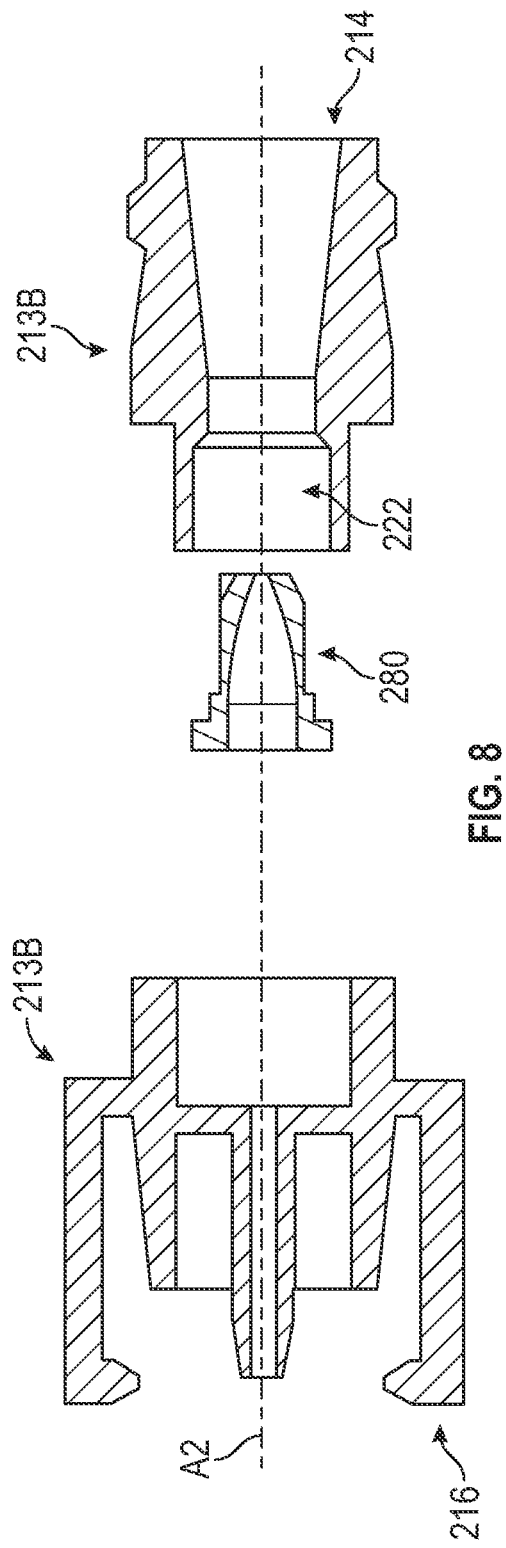
FIG. 8 illustrates an exploded cross-sectional view of a second connector of the fluid connector system, in accordance with aspects of the present disclosure.

Referring to FIG. 8, the second connector 210 can be assembled by inserting the second valve 280 into the body channel 222 of the body. The second valve 280 can be inserted into the body channel 222 through any of the proximal opening 224 at the proximal end of the body or through another opening of the body. In some embodiments, however, the body 212 comprises a distal body portion 213B and a proximal body portion 213A, where the distal and proximal body portions 213B, 213A can be coupled together to form the body channel 222 therebetween. Additionally, the distal and proximal body portions 213B, 213A can be coupled together with the second valve 280 positioned along the body channel 222 therebetween.

The features of the present disclosure provide first and second connectors that can be coupled together to form a fluid pathway therebetween. When coupled together, the features of the present disclosure resist unintentional separation between the first and connectors. However, if the first and connectors are separated, wither unintentionally or intentionally, the fluid pathway for each of the first and connectors become closed or obstructed to prevent fluid loss therefrom. The features of the present disclosure as1 provide that upon separation of the first and second connectors, any of the first and connectors can be cleaned and disinfected, and the first and second connectors can be once again coupled together to form a fluid pathway therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A fluid connector system comprising: a first connector comprising: a housing having a proximal end and a distal end, an inner surface forming a housing channel extending between a proximal opening and a distal opening of the housing, and a first valve positioned in the housing channel; and a second connector comprising: a body having a proximal end and a distal end, an inner surface forming a body channel extending between a proximal opening and a distal opening of the body, and a second valve positioned in the body channel, wherein an outer surface of the distal end of the body forms a protrusion and one or more arm, wherein the one or more arm extends along the protrusion; wherein, when the first and second connectors are coupled together, the one or more arm is engaged against the housing to resist separation of the first and second connectors, and the protrusion extends to the proximal opening of the housing to engage against the first valve and open a fluid passageway through the first and second connectors.

Clause 2. The fluid connector system of Clause 1, wherein the first connector comprises an insert comprising a first end, a second end, an inner surface forming a cavity extending into the second end, and a passage extending through the first end and intersecting the cavity, and wherein the insert is coupled to the proximal end of the housing with the first valve positioned between the cavity of the insert and the proximal opening of the housing.

Clause 3. The fluid connector system of Clause 2, wherein, when the first and second connectors are coupled together the protrusion extends through the passage of the insert.

Clause 4. The fluid connector system of Clause 2, wherein the insert comprises a seal positioned along the passage and configured to engage against the protrusion when the first and second connectors are coupled together.

Clause 5. The fluid connector system of Clause 2, wherein the second end of the insert extends into the proximal opening of the housing.

Clause 6. The fluid connector system of any one of Clauses 1 to 5, wherein the first valve is a check valve configured to permit a fluid to move through the check valve in a direction from the proximal end toward the distal end of the housing, to resist movement of the fluid through the check valve in a direction from the distal end toward the proximal end of the housing.

Clause 7. The fluid connector system of any one of Clauses 1 to 6, wherein an outer surface of the distal end of the housing forms a male luer shape with the housing channel extending therethrough.

Clause 8. The fluid connector system of Clause 7, wherein the distal end of the housing comprises a sleeve having an inner surface that is spaced apart from the outer surface of the male luer.

Clause 9. The fluid connector system of Clause 8, wherein the housing comprises a thread extending along the inner surface of the sleeve.

Clause 10. The fluid connector system of any one of Clauses 1 to 9, wherein an outer surface of the housing comprises a flange that extends radially outward in a direction away from a longitudinal axis extending between the proximal and distal ends of the housing.

Clause 11. The fluid connector system of Clause 10, wherein, when the first and second connectors are coupled together, a portion of the one or more arm is positioned between the flange and the distal end of the housing.

Clause 12. The fluid connector system of Clause 10, wherein the flange comprises a distal-facing surface, the one or more arm comprises a ridge having a proximal facing surface, and wherein, when the first and second connectors are coupled together, the distal-facing surface and the proximal facing surface are coplanar.

Clause 13. The fluid connector system of any one of Clauses 1 to 12, the one or more arm comprises a ridge that extends radially inward in a direction toward a longitudinal axis extending between the proximal and distal ends of the body.

Clause 14. The fluid connector system of any one of Clauses 1 to 13, wherein the second valve is a check valve configured to permit a fluid to move through the check valve in a direction from the proximal end toward the distal end of the body, to resist movement of the fluid through the check valve in a direction from the distal end toward the proximal end of the body.

Clause 15. The fluid connector system of any one of Clauses 1 to 14, wherein the one or more arm comprises a first arm and a second arm, and wherein the first and second arm are spaced apart around a longitudinal axis extending between the proximal and distal ends of the body.

Clause 16. The fluid connector system of any one of Clauses 1 to 15, wherein the one or more arm comprises a circumferential wall having an inner surface that is spaced apart from the outer surface of the protrusion.

Clause 17. A method for providing a fluid connector system, the method comprising: providing a first connector comprising a housing having a proximal end and a distal end, an inner surface forming a housing channel extending between a proximal opening and a distal opening of the housing, and a first valve positioned in the channel of the housing; and providing a second connector comprising a body having a proximal end and a distal end, an inner surface forming a body channel extending between a proximal opening and a distal opening of the body, and a second valve positioned in the channel of the body, wherein an outer surface of the distal end of the body forms a protrusion and one or more arm, wherein the one or more arm extends along the protrusion; wherein the first and second connectors are couplable together such that the one or more arm engages against the housing and the protrusion extends to the proximal opening of the housing to engage against the first valve and open a fluid passageway through the first and second connectors.

Clause 18. The method of Clause 17, wherein the body comprises a proximal portion and a distal portion, and providing the second valve comprises coupling the proximal and distal portions of the body together with the second valve therebetween.

Clause 19. The method of Clause 17, further comprising providing an insert configured to couple to the proximal end of the housing.

Clause 20. The method of Clause 19, wherein providing the first valve comprises coupling the insert to the proximal end of the housing with the first valve positioned therebetween.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid connector system comprising:
   a first connector comprising:
      a housing having a proximal end and a distal end, an inner surface forming a housing channel extending between a proximal opening and a distal opening of the housing, an insert coupled with the proximal opening, and a first valve positioned in the housing channel and between the insert and the housing; and
   a second connector comprising:
      a body having a proximal end and a distal end, an inner surface forming a body channel extending between a proximal opening and a distal opening of the body, and a second valve positioned in the body channel, wherein an outer surface of the distal end of the body forms a protrusion and one or more arm, wherein the one or more arm extends along the protrusion;
   wherein, when the first and second connectors are coupled together, the one or more arm is engaged against the housing to resist separation of the first and second connectors, and the protrusion extends to the proximal opening of the housing to engage against the first valve and open a fluid passageway through the first and second connectors.

2. The fluid connector system of claim 1, wherein the insert comprises a first end, a second end, an inner surface forming a cavity extending into the second end, and a passage extending through the first end and intersecting the cavity, and wherein the insert is coupled to the proximal end of the housing with the first valve positioned between the cavity of the insert and the proximal opening of the housing.

3. The fluid connector system of claim 2, wherein, when the first and second connectors are coupled together the protrusion extends through the passage of the insert.

4. The fluid connector system of claim 2, wherein the insert comprises a seal positioned along the passage and configured to engage against the protrusion when the first and second connectors are coupled together.

5. The fluid connector system of claim 2, wherein the second end of the insert extends into the proximal opening of the housing.

6. The fluid connector system of claim 1, wherein the first valve is a check valve configured to permit a fluid to move through the check valve in a direction from the proximal end toward the distal end of the housing, to resist movement of the fluid through the check valve in a direction from the distal end toward the proximal end of the housing.

7. The fluid connector system of claim 1, wherein an outer surface of the distal end of the housing forms a male luer shape with the housing channel extending therethrough.

8. The fluid connector system of claim 7, wherein the distal end of the housing comprises a sleeve having an inner surface that is spaced apart from the outer surface of the male luer.

9. The fluid connector system of claim 8, wherein the housing comprises a thread extending along the inner surface of the sleeve.

10. The fluid connector system of claim 1, wherein an outer surface of the housing comprises a flange that extends radially outward in a direction away from a longitudinal axis extending between the proximal and distal ends of the housing.

11. The fluid connector system of claim 10, wherein, when the first and second connectors are coupled together, a portion of the one or more arm is positioned between the flange and the distal end of the housing.

12. The fluid connector system of claim 10, wherein the flange comprises a distal-facing surface, the one or more arm comprises a ridge having a proximal facing surface, and wherein, when the first and second connectors are coupled together, the distal-facing surface and the proximal facing surface are coplanar.

13. The fluid connector system of claim 1, wherein the one or more arm comprises a ridge that extends radially inward in a direction toward a longitudinal axis extending between the proximal and distal ends of the body.

14. The fluid connector system of claim 1, wherein the second valve is a check valve configured to permit a fluid to move through the check valve in a direction from the proximal end toward the distal end of the body, to resist movement of the fluid through the check valve in a direction from the distal end toward the proximal end of the body.

15. The fluid connector system of claim 1, wherein the one or more arm comprises a first arm and a second arm, and wherein the first and second arm are spaced apart around a longitudinal axis extending between the proximal and distal ends of the body.

16. The fluid connector system of claim 1, wherein the one or more arm comprises a circumferential wall having an inner surface that is spaced apart from the outer surface of the protrusion.

17. A method for providing a fluid connector system, the method comprising:
   providing a first connector comprising a housing having a proximal end and a distal end, an inner surface forming a housing channel extending between a proximal opening and a distal opening of the housing, an insert coupled with the proximal opening, and a first valve positioned in the channel of the housing and between the insert and the housing; and
   providing a second connector comprising a body having a proximal end and a distal end, an inner surface forming a body channel extending between a proximal opening and a distal opening of the body, and a second valve positioned in the channel of the body, wherein an outer surface of the distal end of the body forms a protrusion and one or more arm, wherein the one or more arm extends along the protrusion;
   wherein the first and second connectors are couplable together such that the one or more arm engages against the housing and the protrusion extends to the proximal opening of the housing to engage against the first valve and open a fluid passageway through the first and second connectors.

18. The method of claim 17, wherein the body comprises a proximal portion and a distal portion, and providing the second valve comprises coupling the proximal and distal portions of the body together with the second valve therebetween.

19. The method of claim 17, wherein providing the first valve comprises coupling the insert to the proximal end of the housing with the first valve positioned therebetween.

* * * * *